United States Patent
Perrey et al.

(10) Patent No.: US 9,392,995 B2
(45) Date of Patent: Jul. 19, 2016

(54) ULTRASOUND IMAGING SYSTEM AND METHOD

(75) Inventors: Christian Fritz Perrey, Zipf (AT); Daniel John Buckton, Zipf (AT); Peter Falkensammer, Zipf (AT)

(73) Assignee: GENERAL ELECTRIC COMPANY, Schenectady, NY (US)

(*) Notice: Subject to any disclaimer, the term of this patent is extended or adjusted under 35 U.S.C. 154(b) by 75 days.

(21) Appl. No.: 13/557,603

(22) Filed: Jul. 25, 2012

(65) Prior Publication Data
US 2014/0031688 A1    Jan. 30, 2014

(51) Int. Cl.
*A61B 8/00*    (2006.01)
*A61B 8/08*    (2006.01)

(52) U.S. Cl.
CPC .............. *A61B 8/5276* (2013.01); *A61B 8/54* (2013.01); *A61B 8/481* (2013.01); *A61B 8/483* (2013.01)

(58) Field of Classification Search
USPC .................................. 600/438, 443; 382/128
See application file for complete search history.

(56) References Cited

U.S. PATENT DOCUMENTS

| | | | |
|---|---|---|---|
| 5,873,830 A | 2/1999 | Hossack et al. | |
| 6,508,768 B1 | 1/2003 | Hall et al. | |
| 6,558,324 B1* | 5/2003 | Von Behren et al. | 600/440 |
| 7,223,241 B2 | 5/2007 | Radulescu | |
| 8,235,900 B2* | 8/2012 | Hao | 600/437 |
| 2002/0072670 A1* | 6/2002 | Chenal et al. | 600/449 |
| 2005/0033173 A1* | 2/2005 | Von Behren et al. | 600/443 |
| 2007/0078344 A1* | 4/2007 | Rafter | 600/450 |
| 2010/0168573 A1* | 7/2010 | Sherrill | 600/440 |
| 2010/0249591 A1 | 9/2010 | Heimdal et al. | |
| 2010/0249592 A1 | 9/2010 | Langeland et al. | |
| 2013/0225986 A1* | 8/2013 | Eggers et al. | 600/425 |

* cited by examiner

*Primary Examiner* — Katherine Fernandez
*Assistant Examiner* — Ellsworth Weatherby (57) ABSTRACT

An ultrasound imaging system and method includes acquiring motion data for a region-of-interest (ROI). The system and method includes calculating a quality parameter based on the motion data, wherein the quality parameter represents an amount of unwanted motion in the ROI. The system and method includes performing an action based on the quality parameter.

3 Claims, 5 Drawing Sheets

ULTRASOUND IMAGING SYSTEM AND METHOD

FIELD OF THE INVENTION

This disclosure relates generally to an ultrasound imaging system and method for calculating a quality parameter based on motion data.

BACKGROUND OF THE INVENTION

Conventional 2D matrix array probes coupled with current generation ultrasound systems are not fast enough to acquire clinically suitable volume sizes with the required temporal and spatial resolution for applications such as fetal heart imaging. According to current practice, a method was developed that divides the desired region-of-interest (ROI) into two or more partial volumes. Data is collected over each of these partial volumes over multiple heart cycles and then an entire 4D volume sequence is reconstructed by spatially and temporally stitching together volumes acquired from each of the partial volumes. The resulting 4D ultrasound data includes data from multiple cardiac phases for all of the partial volumes.

Relative motion between the anatomy in the ROI and the probe may result in motion artifacts that significantly reduce the quality of the 4D ultrasound data. In order to acquire and generate a high-quality image, it is important that the position of the ultrasound probe does not move with respect to the anatomical structure, such as a heart, being imaged. If relative movement occurs during acquisition, the resulting 4D ultrasound data may contain spatial artifacts and/or temporal artifacts visible as a discontinuity when viewing images generated from the 4D ultrasound data.

Since motion during the acquisition may result in image artifacts, it is important to acquire 4D ultrasound with as little unwanted motion as possible. When acquiring 4D ultrasound data of a heart as a group of partial volumes, it is necessary to perform the acquisition over multiple cardiac cycles. If any unwanted motion occurs, it will typically be detectable only when viewing a cine image, or a sequence of images over time, after the acquisition has been completed. If the artifact is severe enough, it may render the 4D ultrasound data unusable. If this is the case, it may be necessary for an operator to reacquire the 4D ultrasound data one or more times. According to conventional systems, the operator may be forced to iteratively complete a number of acquisitions before acceptable 4D ultrasound data has been successfully acquired. Repeated acquisitions waste time and are an inconvenience for both the operator and the patient.

For these and other reasons an improved method and ultrasound imaging system for acquiring 4D ultrasound data are desired.

BRIEF DESCRIPTION OF THE INVENTION

The above-mentioned shortcomings, disadvantages and problems are addressed herein which will be understood by reading and understanding the following specification.

In an embodiment, a method of ultrasound imaging includes dividing a region-of-interest (ROI) into a plurality of partial volumes. The method includes acquiring 4D ultrasound data from each of the plurality of partial volumes and acquiring motion data from at least one of the plurality of partial volumes during the process of acquiring the 4D ultrasound data. The method includes calculating a quality parameter during the process of acquiring the 4D ultrasound data. The quality parameter is based on the motion data and represents an amount of unwanted motion in the ROI. The method includes performing an action based on the quality parameter.

In an embodiment, a method of ultrasound imaging includes dividing a region-of-interest into a plurality of partial volumes and acquiring motion data from the ROI. The method includes calculating a quality parameter based on the motion data. The quality parameter indicates an amount of unwanted motion in the ROI. The method includes acquiring 4D ultrasound data for each of the plurality of partial volumes if the quality parameter is acceptable.

In another embodiment, an ultrasound imaging system includes a probe, a display device, and a processor in electronic communication with the probe and the display device. The processor is configured to divide a region-of-interest (ROI) into a plurality of partial volumes and acquire 4D ultrasound data for each of the plurality of partial volumes. The processor is configured to acquire motion data from at least one of the plurality of partial volumes during the process of acquiring the 4D ultrasound data. The processor is configured to calculate a quality parameter based on the motion data, determine if the quality parameter is acceptable, and perform an action based on the quality parameter.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
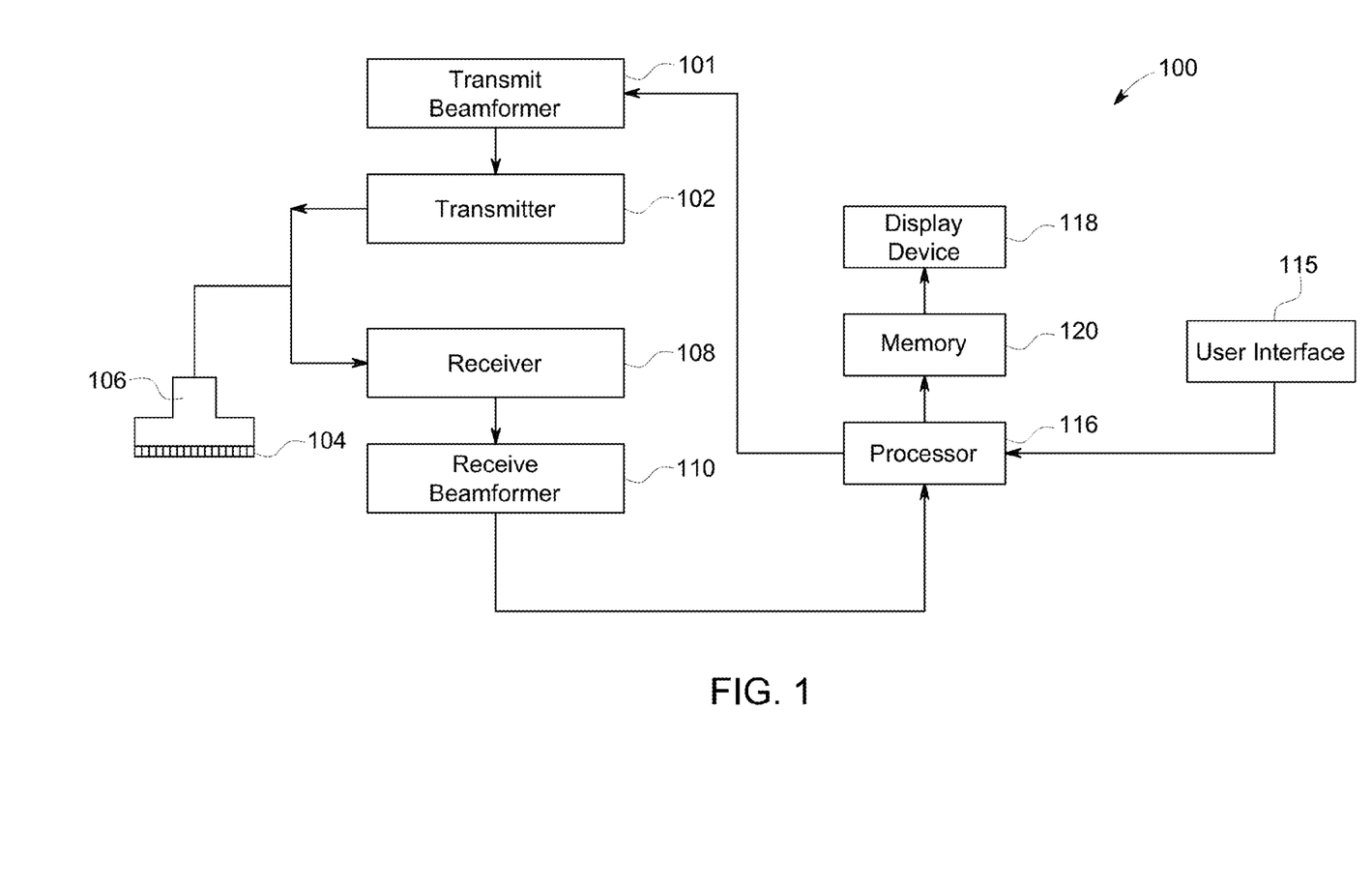
FIG. 1 is a schematic diagram of an ultrasound imaging system in accordance with an embodiment.

FIG. 1 is a schematic diagram of an ultrasound imaging system 100 in accordance with an embodiment. The ultrasound imaging system 100 includes a transmit beamformer 101 and a transmitter 102 that drive elements 104 within a probe 106 to emit pulsed ultrasonic signals into a body (not shown). According to an embodiment, the probe 106 may be a 2D matrix array probe. However, any other type of probe capable of acquiring four-dimensional (4D) ultrasound data may be used according to other embodiments. For purposes of this disclosure, the term four-dimensional ultrasound data, or 4D ultrasound data, is defined to include ultrasound data including multiple 3D volumes acquired over a period of time. The 4D ultrasound data contains information showing how a 3D volume changes over time. Still referring to FIG. 1, the pulsed ultrasonic signals are back-scattered from structures in the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. According to some embodiments, the probe 106 may contain electronic circuitry to do all or part of the transmit and/or the receive beamforming. For example, all or part of the transmit beamformer 101, the transmitter 102, the receiver 108 and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. A user interface 115 may be used to control operation of the ultrasound imaging system 100, including, to control the input of patient data, to change a scanning or display parameter, and the like.

The ultrasound imaging system 100 also includes a processor 116 to control the transmit beamformer 101, the transmitter 102, the receiver 108 and the receive beamformer 110. The processor 116 is in electronic communication with the probe 106. For purposes of this disclosure, the term "electronic communication" may be defined to include both wired and wireless connections. The processor 116 may control the probe 106 to acquire data. The processor 116 controls which of the elements 104 are active and the shape of a beam emitted from the probe 106. The processor 116 is also in electronic communication with a display device 118, and the processor 116 may process the data into images for display on the display device 118. The processor 116 may include a central processor (CPU) according to an embodiment. According to other embodiments, the processor 116 may include other electronic components capable of carrying out processing functions, such as a digital signal processor, a field-programmable gate array (FPGA) or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment the demodulation can be carried out earlier in the processing chain. The processor 116 is adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without any intentional delay. For example, an embodiment may acquire images at a real-time rate of 7-20 volumes/sec. However, it should be understood that the real-time volume-rate may be dependent on the length of time that it takes to acquire each volume of data for display. Accordingly, when acquiring a relatively large volume of data, the real-time volume-rate may be slower. Thus, some embodiments may have real-time volume-rates that are considerably faster than 20 volumes/sec while other embodiments may have real-time volume-rates slower than 7 volumes/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data prior to displaying an image. It should be appreciated that other embodiments may use a different arrangement of processors.

The ultrasound imaging system 100 may continuously acquire data at a volume-rate of, for example, 10 Hz to 30 Hz. Images generated from the data may be refreshed at a similar frame-rate. Other embodiments may acquire and display data at different rates. For example, some embodiments may acquire data at a volume-rate of less than 10 Hz or greater than 30 Hz depending on the size of the volume and the intended application. A memory 120 is included for storing processed volumes of acquired data. In an exemplary embodiment, the memory 120 is of sufficient capacity to store at least several seconds worth of volumes of ultrasound data. The volumes of data are stored in a manner to facilitate retrieval thereof according to its order or time of acquisition. The memory 120 may comprise any known data storage medium.

Optionally, embodiments of the present invention may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed by other or different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate and combinations thereof, and the like. The image beams and/or volumes are stored and timing information indicating a time at which the data was acquired in memory may be recorded. The modules may include, for example, a scan conversion module to perform scan conversion operations to convert the image volumes from beam space coordinates to display space coordinates. A video processor module may be provided that reads the image volumes from a memory and displays an image in real time while a procedure is being carried out on a patient. A video processor module may store the images in an image memory, from which the images are read and displayed.

Figure 2:
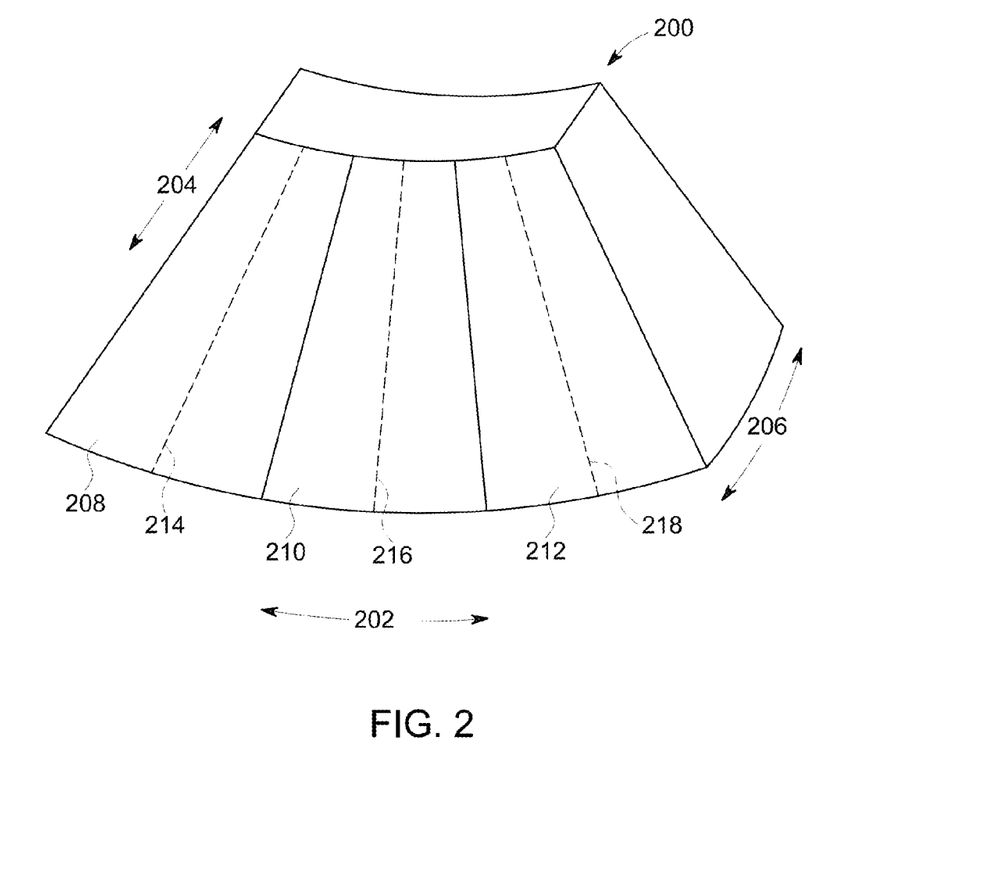
FIG. 2 is a schematic representation of a volume in accordance with an embodiment.

FIG. 2 is a schematic representation of a volume according to an embodiment. The volume 200 may be acquired by the probe 106 shown in FIG. 1 and, as mentioned previously, the probe 106 may be a 2D matrix array. The volume 200 may be defined based on its dimensions with respect to the probe 106. For example, an elevation direction 202, a depth direction 204, and an azimuth direction 206 are all shown with respect to the volume 200. As will be described in detail hereinafter, the volume 200 includes a first partial volume 208, a second partial volume 210, and a third partial volume 212.

Figure 3:
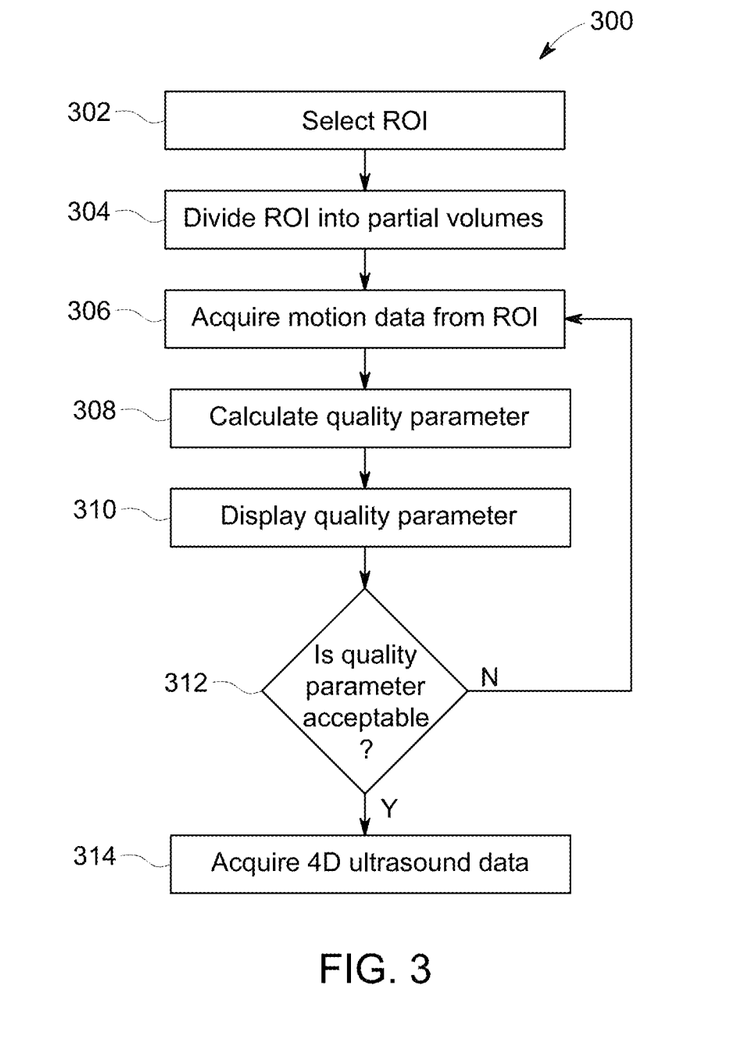
FIG. 3 is a flow chart of a method in accordance with an embodiment.

FIG. 3 is a flow chart of a method in accordance with an exemplary embodiment. The individual blocks of the flow chart represent steps that may be performed in accordance with the method 300. Additional embodiments may perform the steps shown in a different sequence and/or additional embodiments may include additional steps not shown in FIG. 3. The technical effect of the method 300 is the calculation of a quality parameter based on motion data acquired from a region-of-interest, referred to hereinafter as an ROI. The method 300 will be described according to an exemplary embodiment where the method 300 is implemented by the processor 116 of the ultrasound imaging system 100 of FIG. 1. Additionally, the method 300 will be described according to an embodiment where 4D ultrasound data of a fetal heart is acquired in three partial volumes. It should be appreciated by those skilled in the art that the method 300 may be used to acquire 4D ultrasound data of other organs or anatomical structures as well. The method 300 may also be used to acquire 4D ultrasound data of an ROI with a different number of partial volumes. For example, the method 300 may be used to acquire 4D ultrasound data of an ROI with as few as 2 partial volumes or an ROI with more than 3 partial volumes.

Referring to FIGS. 1, 2 and 3, at step 302, the user selects an ROI, such as the volume 200. The user may select the extent of the ROI based on inputs through the user interface 115. The ROI may be selected to show some or all of an organ or tissue that is being examined. According to an exemplary embodiment, the ROI may be selected to include a fetal heart. According to other embodiment, the ROI may be selected to include other organs, including an adult heart.

At step 304, the processor 116 divides the ROI into a plurality of partial volumes, such as the first partial volume 208, the second partial volume 210, and the third partial volume 212. The processor 116 may determine how to divide the volume 200 into partial volumes based on the desired characteristics of the 4D ultrasound data, the technical specifications of the ultrasound imaging system 100, or based on user input received through the user interface 115. For example, the user may select the desired characteristics of the 4D ultrasound data through the user interface 115. These characteristics may include variables such as temporal resolution, line density, total acquisition time, and the like. The processor 116 may compare the desired characteristics of the 4D ultrasound data with the technical specifications of the ultrasound imaging system 100. For example, according to the exemplary embodiment where the ROI includes a fetal heart, the processor 116 may calculate how many partial volumes are necessary in order to get the desired line density and temporal resolution, or refresh rate, for the entire ROI. According to the exemplary embodiment, the processor 116 divides the ROI into 3 partial volumes. However, it should be appreciated by those skilled in the art, that the ROI may be divided into a different number of partial volumes in accordance with other embodiments. The shapes and/or orientation of the partial volumes may be different as well according to other embodiments.

Next, at step 306, the processor 116 controls the acquisition of motion data for the ROI. According to an exemplary embodiment, the processor 116 may control the probe 106 to acquire M-mode data for one or more of the partial volumes 208, 210, 212. For example, M-mode data may be acquired for the first partial volume 208 along the first line 214, M-mode data may be acquired for the second partial volume 210 along the second line 216, and M-mode data may be acquired for the third partial volume 212 along the third line 218. According to other embodiments, motion data may be acquired from only one of the partial volumes during the method 300.

At step 308, the processor 116 calculates a quality parameter based on the motion data acquired at step 306. According to an embodiment, the processor 116 may calculate the quality parameter by analyzing the motion data for any unwanted movement. An exemplary method of calculating a quality parameter will be described hereinafter with respect to FIG. 4. The processor 116 then displays a quality parameter calculated based on the motion data at step 310. Next, at step 312 the processor 116 determines if the quality parameter is acceptable. If the quality parameter is unacceptable, the method 300 returns to step 306. Steps 306, 308, 310, and 312 may be repeated multiple times until the quality parameter based on the most recently acquired motion data is acceptable.

However, if the processor 116 determines that the quality parameter is acceptable at step 312, thus indicating that the unwanted movement within the ROI is less than a threshold amount, the method 300 advances to step 314 where 4D ultrasound data of the ROI is acquired. According to other embodiments, step 310 may be omitted, and the processor 116 may determine if the quality parameter is acceptable without displaying the quality parameter.

Figure 4:
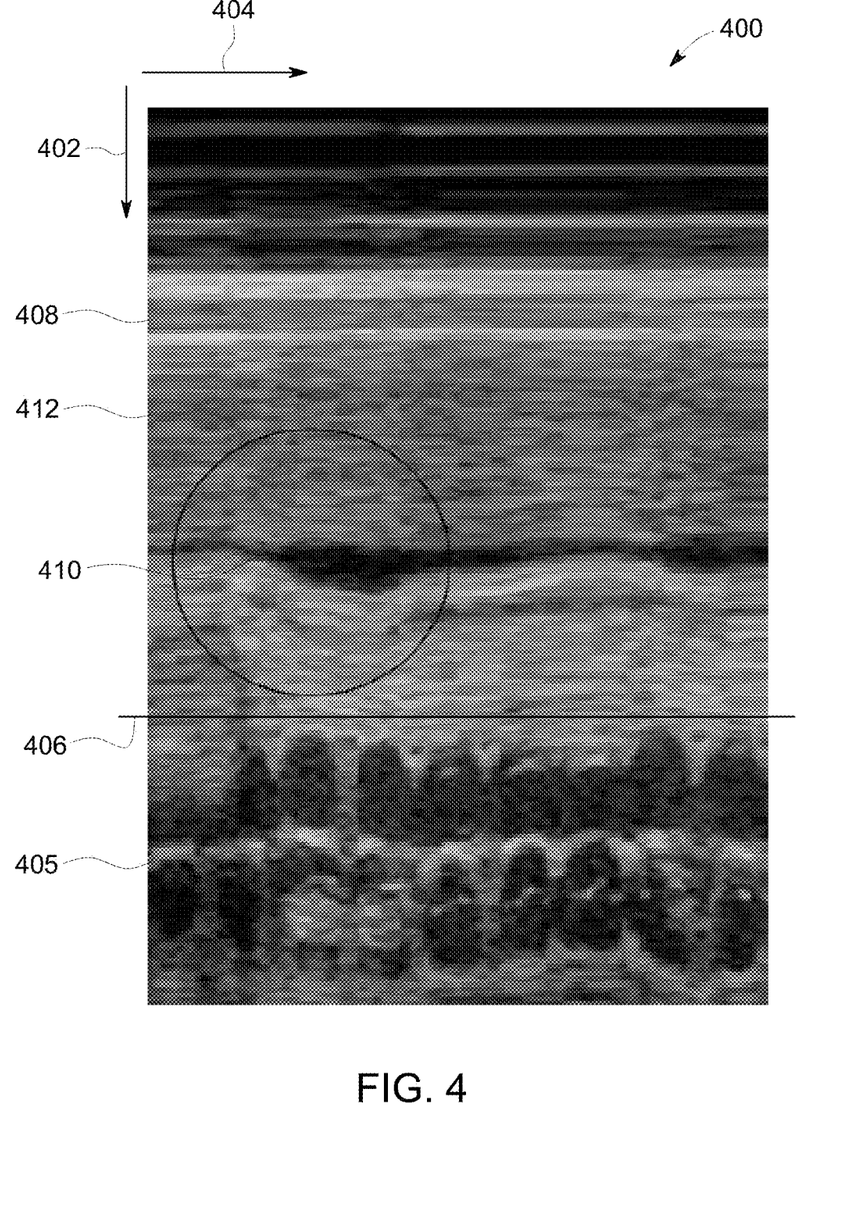
FIG. 4 is a graph showing an M-mode trace over time in accordance with an embodiment.

FIG. 4 is a graph showing an M-mode trace over time in accordance with an embodiment. The graph 400 represents depth in a y-direction 402 and slow time in an x-direction 404. Each column of pixels in the graph 400 represents a single M-mode acquisition or trace. An M-mode trace represents a single line of ultrasound data and each trace is represented in the graph 400. The slow time along the x-direction 404 increases from left to right, which means that the graph 400 show how an M-mode trace varies with time. The graph 400 may depict an M-mode trace acquired along any one of the first line 214, the second line 216, or the third line 218 according to an exemplary embodiment. The graph 400 shows an embodiment where the M-mode trace was acquired of a cardiac region over a period of multiple cardiac cycles. A first portion 405 of the graph 400 below line 406 shows periodic motion. According to an embodiment, this periodic motion may correspond to the rhythmic beating of a patient's heart. There are approximately 10 cardiac cycles of motion data included in the first portion 405. The first portion 405 of the graph 400 depicts a portion of the heart that exhibits periodic motion in healthy patients. Therefore, it is not desirable to analyze the first portion 405 for unwanted motion. However, a second portion 408 above the line 406, includes anatomy that is not experiencing periodic motion consistent with regular physiological motion. It is, therefore, desirable to analyze the portion of the M-mode data represented by the second portion 408 of the graph 400 for motion.

According to an embodiment, the processor 116 may implement a Fast Fourier Transform on the motion data in order to separate the portion of the data experiencing periodic motion, like that represented by the first portion 405, from the portion of the data that is not experiencing periodic motion, such as that represented by the second portion 408. The Fast Fourier Transform represents the motion data in a frequency domain and enables the processor 116 to easily identify portions of the data that exhibit periodic motion within the range of frequencies expected by periodic physiological motion, such as a beating heart. Likewise, the processor 116 can easily identify motion data corresponding to regions that do not exhibit periodic physiological motion. According to the example shown in the graph 400, the processor 116 would identify the motion data below the line 406 as exhibiting periodic motion and the motion data about the line 406 as not exhibiting periodic motion.

Then, the processor 116 may analyze the data represented by the second portion 408 above the line 406. While still in the frequency domain, the processor 116 may analyze the motion data to identify any unwanted movement. Assuming that the tissue is not moving and that the probe 106 is held in a stationary position, the motion data represented by the second portion 408 of graph 400 should not show significant motion. Therefore, the processor 116 may search within the motion data for changes within this subset of the motion data. Those skilled in the art will realize that it is rarely possible to have absolutely zero movement between the probe 106 and the anatomy being imaged. Therefore, it may be necessary to adjust a threshold or filter to only identify movements above a certain magnitude as likely to have been caused by motion. The setting of this threshold or filter may be determined based on experimental studies.

The graph 400 includes a region 410 showing unwanted motion. Regarding the second portion 408, there should minimal variations in a horizontal direction, which represents slow time. However, at the region 410, a significant discontinuity is visible. The region 410 includes M-mode data that was acquired while there was relative movement between the probe 106 and the tissue being examined at depth 412. While the second region 408 is graphically represented on the graph 400, it should be appreciated that the processor 116 may identify that there is a region showing unwanted motion by examining the Fast Fourier Transform of the motion data. It is not necessary for the processor 116 to generate a graph such as the graph 400 in order to identify unwanted motion.

According to an embodiment, the analysis described hereinabove with respect to FIG. 4 may be repeated for the motion data acquired for each of the partial volumes. In other words, since motion data may be acquired along lines 214, 216, and 218, the processor 116 may independently analyze the motion data acquired along line 214, line 216, and line 218. As described previously, the motion data acquired along the first line 214 represents the first partial volume 208, the motion data acquired along the second line 216 represents the second partial volume 210, and the motion data acquired along the third line 218 represents the third partial volume 212. Therefore, by analyzing motion data from each of the partial volumes, the processor 116 may determine if there is unwanted motion in any one of the partial volumes.

It should be appreciated by those skilled in the art that analyzing M-mode data in the frequency domain, as described above, is only one exemplary way of analyzing the motion data for unwanted motion and that other embodiments may use other techniques of identifying unwanted motion in the motion data.

Referring back to FIG. 3, at step 310, the processor 116 displays the quality parameter calculated at step 308 on the display device 118. The quality parameter may be displayed as an icon or as a color-coded indicator according to various embodiments. For example, a first icon may be displayed if the quality parameter is within an acceptable range and a second icon may be displayed if the quality parameter is outside of an acceptable range. The quality parameter may include both color-coding and icon shape in order to identify the status of the quality parameter. The user may watch the quality parameter displayed on the display device for feedback regarding whether or not the unwanted motion between the ROI and the probe 106 is within an acceptable level.

Figure 5:
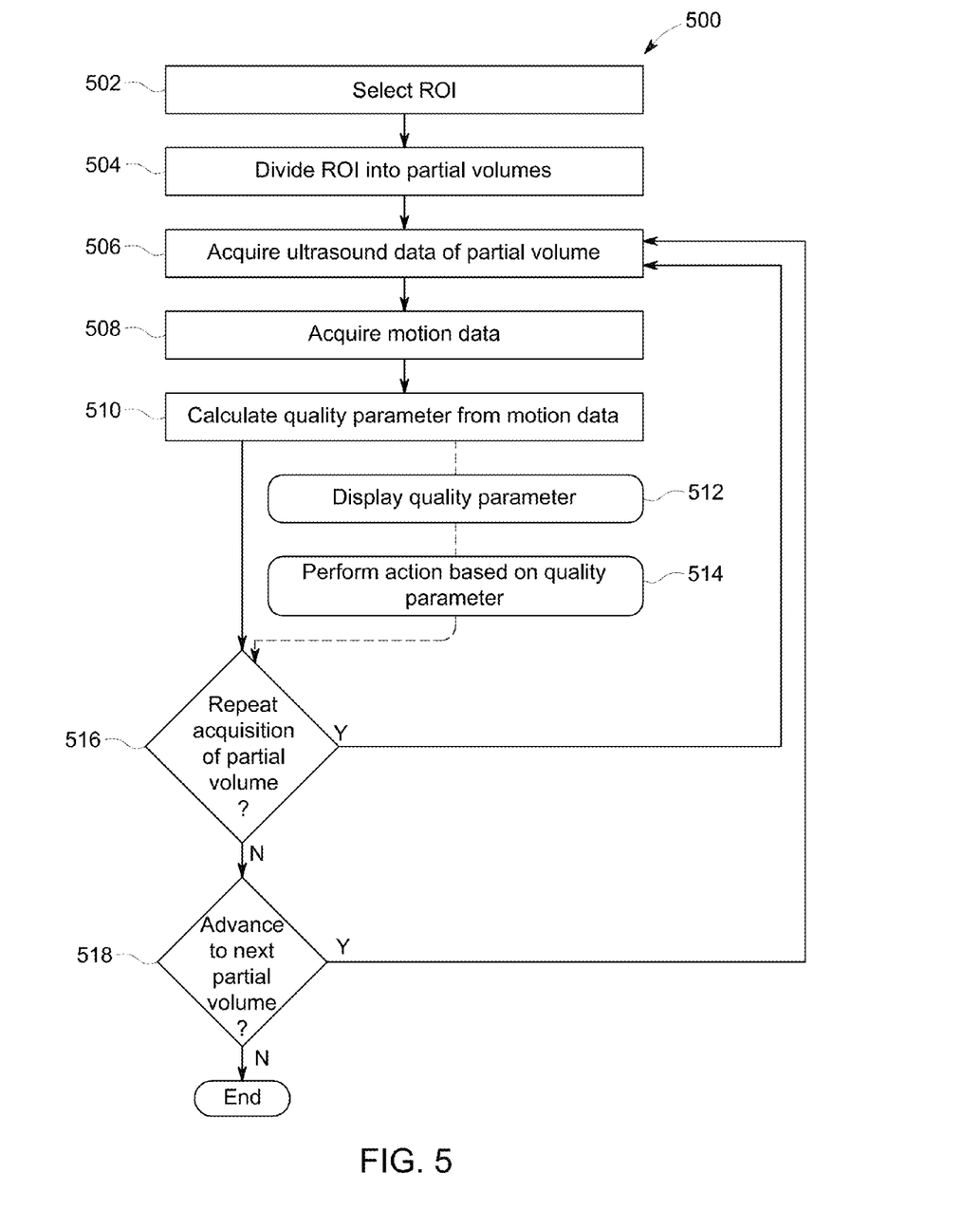
FIG. 5 is a flow chart of a method in accordance with an embodiment.

FIG. 5 is a flow chart of a method in accordance with an exemplary embodiment. The individual blocks of the flow chart represent steps that may be performed in accordance with the method 500. Additional embodiments may perform the steps shown in a different sequence and/or additional embodiments may include additional steps not shown in FIG. 5. The technical effect of the method 500 is the calculation of a quality parameter based on motion within the ROI. The method 500 will be described according to an exemplary embodiment where the method is implemented by the processor 116 of the ultrasound imaging system 100 of FIG. 1. Additionally, the method 500 will be described according to an embodiment where 4D ultrasound data of a heart is acquired in three partial volumes.

Referring to FIGS. 1, 2 and 5, at step 502, the user selects an ROI, such the ROI. The user may select the extent of the ROI based on inputs through the user interface 115.

At step 504, the processor 116 divides the ROI into a plurality of partial volumes, such as the first partial volume 208, the second partial volume 210, and the third partial volume 212. The processor 116 may determine how to divide the ROI into partial volumes based on the desired characteristics of the 4D ultrasound data, the technical specifications of the ultrasound imaging system 100, or based on user input through the user interface 115. According to an exemplary embodiment, the ROI may include a fetal heart. The processor 116 may calculate how many partial volumes are necessary in order to get the desired line density and temporal resolution, or refresh rate, for the entire ROI. It should be appreciated by those skilled in the art, that the ROI may be divided into a different number of partial volumes in accordance with other embodiments. The shapes and/or orientation of the partial volumes may be different as well according to other embodiments.

Next, at step 506, the processor 116 controls specific components in the ultrasound imaging system 100 in order to acquire ultrasound data for one of the partial volumes. According to an embodiment, the processor 116 controls the transmit beamformer 101, the transmitter 102, the probe 106, the receiver 108, and the receive beamformer 110 to start by acquiring a volume of ultrasound data of the first partial volume 208. Next, after acquiring a volume of data of the first partial volume 208, the method 300 advances to step 508, where the processor 116 controls the acquisition of motion data for at least one of the partial volumes 208, 210, 212. According to an exemplary embodiment, the processor 116 may control the probe 106 to acquire one or more lines of M-mode data or synthetic M-mode data for each of the partial volumes 208, 210, 212. For example, M-mode data may be acquired for the first partial volume 208 along the first line 214, M-mode data may be acquired for the second partial volume 210 along the second line 216, and M-mode data may be acquired for the third partial volume 212 along the third line 218. It should be appreciated that other embodiments may acquire M-mode data along lines other than the lines shown in FIG. 2. Additionally, some embodiments may acquire motion data along two or more lines within each partial volume. For example, an embodiment may acquire motion data along multiple lines oriented in different directions in order to detect motion in the different directions. According to yet other embodiment, step 508 may include acquiring motion data along only a single line during each repetition of steps 506, 508, 510, 512, 514, 516, and 518.

According to other embodiments, the motion data for the ROI may be acquired according to different techniques. For example, the processor 116 may generate synthetic M-mode data based on one or more volumes within the ultrasound data. For the purposes of this disclosure, the term "synthetic M-mode data" is defined to include extracting a single line of ultrasound data from a plurality of frames or a plurality of volumes acquired over a period of time. The synthetic M-mode data includes that single line over a period of time, just like normal M-mode data. However, instead of being acquired individually, the synthetic M-mode data is derived from 2D, 3D, or 4D ultrasound data. Additionally, according to other embodiments, the motion data may be acquired through the use of a correlation technique. The processor 116 may compare each volume of the 4D ultrasound data with previously acquired volumes and implement a correlation technique in order to detect the amount of movement between adjacent volumes. For example, a technique such as block-modeling may be used in order to detect how much movement has occurred between adjacent volumes. It should be appreciated by those skilled in the art that the term "adjacent" may refer to spatially adjacent volumes, temporally adjacent volumes, or volumes that are adjacent with respect to phase. Block-modeling includes dividing each acquired volume into a plurality of smaller sub-volumes and then tracking how each of the sub-volumes move over time. Acquiring motion data based on either synthetic M-mode data or correlation techniques do not require the acquisition of additional ultrasound data. Instead, the processor 116 may acquire the motion data directly from the 4D ultrasound data acquired at step 508.

At step 510, the processor 116 calculates a quality parameter from the motion data. Steps 512 and 514 are optional steps that may optionally be performed during the method 500. Additional details about step 510 and optional steps 512 and 514 will be described hereinafter.

Next, at step 516, the processor 116 determines if it is desired to acquire additional ultrasound data of the same partial volume for which ultrasound data was acquired during step 506. If it is desirable to acquire additional ultrasound data for the partial volume, then the method 500 returns to step 506. According to an embodiment, it is desirable to acquire ultrasound data for each partial volume over a period of time that is at least as long as one cardiac cycle long in order to acquire ultrasound data representing the partial volume at a plurality of different cardiac phases. Therefore, the processor 116 may use an estimated cardiac rate in order to determine if it is desirable to acquire additional ultrasound data of a particular partial volume at step 516. In an exemplary embodiment, the method 500 iteratively repeats steps 506, 508, and 510, optional steps 512 and/or 514, and step 516 during an amount of time at least as long as a cardiac cycle. Each time the method 500 repeats steps 506, 508, and 510, optional steps 512 and/or 514, and step 516, a new volume of ultrasound data for a specific partial volume is acquired. For example, the method 300 may iteratively cycle through steps 506, 508, and 510, optional steps 512 and/or 514, and step 516 in order to acquire multiple volumes of ultrasound data of the first partial volume 208. Each of the volumes of ultrasound data represents a partial volume, such as the first partial volume 208, at a different point in time. Collectively, the multiple volumes of ultrasound data of each partial volume are referred to as 4D ultrasound data for purposes of this disclosure since they show how the partial volume changes over time. The term "4D ultrasound data" is also defined to include ultrasound data showing change over a period of time for a larger volume, such as the whole ROI for purposes of this disclosure. By repeating steps 506, 508, and 510, optional steps 512 and 514, and step 516 multiple times, the method 500 acquires first 4D ultrasound data of the first partial volume 208.

However, once enough ultrasound data has been acquired for the first partial volume 208, the method 300 advances to the next partial volume at step 518. Since, according to an exemplary embodiment, 4D ultrasound data of the first partial volume 208 has already been acquired, the processor 116 decides to advance to the next partial volume, which may be the second partial volume 210 according to an embodiment. Then the method 500 iteratively repeats steps 506, 508, 510, optional steps 512 and 514, and step 516 in order to acquire second 4D ultrasound data for the second partial volume 210 for a length of time at least as long as a cardiac cycle. Then, at step 518, when enough 4D ultrasound data has been acquired for the second partial volume 210, the method 500 advances to the next partial volume, which may be the third partial volume 212 according to an exemplary embodiment.

The method 500 then iteratively repeats steps 506, 508, 510, optional steps 512 and 514, and step 516 in order to acquire 4D ultrasound data of the third partial volume 212 for a period of time that is at least as long as the patient's cardiac cycle. This results in the acquisition of 4D ultrasound data for the third partial volume 212 representing a plurality of different phases of the patient's cardiac cycle.

At step 510, the processor 116 calculates a quality parameter based on the motion data. The quality parameter is an indicator of the amount of unwanted motion occurring between the probe 106 and the ROI. The processor 116 may use many different techniques to calculate the quality parameter. The processor 116 may either calculate the quality parameter for each partial volume independently, or the processor 116 may calculate the quality parameter for the ROI as a whole. According to an exemplary embodiment, the processor 116 may calculate the quality parameter according to the method that was previously described with respect to FIG. 4. Calculating the quality parameter may include assigning a score based on the amount of unwanted motion detected in the motion data.

Those skilled in the art will appreciate that the method 500 includes two loops. An inner loop includes steps 506, 508, 510, optional step 512, optional step 514, and step 516. And, an outer loop includes steps 506, 508, 510, optional step 512, optional step 514, step 516, and step 518. Each time the method 500 cycles through either the inner or the outer loop, additional motion data is acquired at step 508. The quality parameter calculated at step 510 may be displayed at optional step 512. According to another embodiment, multiple quality parameters may be calculated, where each quality parameter represents the motion data within only one of the partial volumes. The quality parameter may be displayed as an icon, a color-coded indicator, or other types of graphical and/or numerical indicators. Additionally, according to other embodiments, the value of the quality parameter may result in an audible warning if it is outside of an acceptable range. Since step 512 is optional, the quality parameter may not be displayed during each time the method 500 performs the inner or outer loop. Step 512, may only be performed after the method 500 has performed the inner loop and/or the outer loop a predetermined number of times. For example, according to an embodiment, the quality parameter may be displayed after the acquisition of each partial volume, after the acquisition of the whole ROI, or after the acquisition of 4D ultrasound data for the whole ROI according to various embodiments. According to other embodiments, the quality parameter may be updated and displayed with each pass through either the inner loop or the outer loop of the method 500. It should be appreciated by those skilled in the art that the display of the quality parameter at step 512 results in the display of the quality parameter during the process of acquiring 4D ultrasound data. By displaying the quality parameter at step 512, the user is presented with real-time feedback regarding the amount of unwanted motion during the process of acquiring 4D ultrasound data. For example, the user may monitor the displayed quality parameter while acquiring the 4D ultrasound data. This way, the user may receive feedback regarding excessive motion during the process of acquiring the 4D ultrasound data of the ROI. By displaying the quality parameter during the process of acquiring the 4D ultrasound data, the user may receive feedback very quickly regarding unwanted motion within any of the partial volumes. This is a marked improvement over conventional techniques where the user would not be able to identify that there was too much motion until completing the acquisition of 4D ultrasound data for the whole ROI. Additionally, with conventional techniques, the user would have to manually identify the artifact. In contrast, the method 500 provides the user with the motion data very quickly through the quality parameter, thus saving both the user and the patient significant time in specific situations. According to yet other embodiments, step 512 may be omitted and the method may not include the display of a quality parameter.

At optional step 514, an action is performed based on the quality parameter. The action performed at step 514 may vary depending upon the status of the quality parameter. If the quality parameter is acceptable, the action may include generating an image based on the 4D ultrasound data and displaying the image on the display device 118. The image based on the 4D ultrasound data may be generated by first combining the 4D ultrasound data for each of the partial volumes according to known techniques. The image may include a slice from within the ROI, a volume-rendering based on some or all of the ROI, or any other type of image that is generated from some or all of the 4D ultrasound data acquired at step 506. If the quality parameter is acceptable, thus indicating limited or no unwanted motion in the partial volumes, then the action may include stopping the acquisition of 4D ultrasound data and/or displaying an image based on the 4D ultrasound data. It should be appreciated that, according to the embodiment shown in the method 500, steps 512 and 514 may be performed in real-time during the process of acquiring 4D ultrasound data of the ROI. If 4D ultrasound data has been acquired for each of the partial volumes over the desired period of time, and if the quality parameter is acceptable, it may not be necessary to acquire any additional 4D ultrasound data.

Different exemplary actions may be performed at step 514 if the quality parameter is unacceptable. An unacceptable quality parameter would indicate that there was too much unwanted motion in one or more of the partial volumes. According to an embodiment, the action may include continuing to acquire 4D ultrasound data until the quality parameter is acceptable. This may be accompanied by repeating steps 506, 508, 510, optional steps 512 and 514, and step 516 until the quality parameter is acceptable. According to another embodiment, if the quality parameter indicates excessive unwanted motion, the action performed at step 514 may include stopping the acquisition of 4D ultrasound data so that the user may start a new acquisition. Additionally, the user may want to reposition the probe 106 and wait until the patient stops moving before acquiring additional 4D ultrasound data. The action performed at step 514 may either be performed automatically by the processor 116, or the action may be performed manually by the user.

According to another embodiment, if the quality parameter is unacceptable, the processor 116 may perform the action of controlling the probe 106 to continue acquiring 4D ultrasound data of the ROI. It should be appreciated that according to some embodiments, the processor 116 may calculate the quality parameter, evaluate the quality parameter, and perform an action based on the quality parameter during the process of acquiring 4D ultrasound data of each of the partial volumes. For example, the processor may perform the action of displaying an image with an icon or indicator to represent the quality parameter during the process of acquiring 4D ultrasound data of the ROI.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A method for ultrasound imaging a region-of-interest, the method comprising:
    dividing, using a processor, the region-of-interest into a plurality of partial volumes;
    acquiring four-dimensional (4D) ultrasound data from each of the plurality of partial volumes with a probe in a substantially stationary position, where the 4D ultrasound data from each of the plurality of partial volumes comprises multiple three-dimensional (3D) volumes acquired over a period of time, and where each 3D volume comprises a plurality of slices acquired from distinct positions;
    acquiring motion data from each of the plurality of partial volumes while the probe is in the substantially stationary position, where the motion data for each partial volume represents an amount of motion between the probe and tissue within each partial volume;
    calculating, using the processor, a quality parameter for each partial volume based on the motion data;
    determining, using the processor, if the quality parameter is unacceptable for one of the plurality of partial volumes because the amount of motion between the probe and the tissue within the one of the plurality of partial volumes exceeds a threshold;
    automatically acquiring additional 4D ultrasound data for the one of the plurality of partial volumes in response to determining that the quality parameter is unacceptable;
    generating, using the processor, an image of the region-of-interest based on both a portion of the 4D ultrasound data and the additional 4D ultrasound data; and displaying the image.

2. The method of claim 1, wherein said acquiring the motion data comprises acquiring one of M-mode data and synthetic M-mode data for each of the plurality of partial volumes.

3. The method of claim 1, wherein said acquiring the motion data comprises implementing a correlation technique on the 4D ultrasound data.

* * * * *